US010058672B2

(12) United States Patent
Matsubara et al.

(10) Patent No.: US 10,058,672 B2
(45) Date of Patent: Aug. 28, 2018

(54) GAS SUPPLY MASK APPARATUS

(71) Applicant: Atom Medical Corporation, Tokyo (JP)

(72) Inventors: Kazuo Matsubara, Tokyo (JP); Terumi Matsubara, Saitama (JP); Kenji Kobayashi, Saitama (JP); Shinichi Kobayashi, Saitama (JP)

(73) Assignee: Atom Medical Corporation, Tokyo (JP)

( * ) Notice: Subject to any disclaimer, the term of this patent is extended or adjusted under 35 U.S.C. 154(b) by 524 days.

(21) Appl. No.: 14/717,163

(22) Filed: May 20, 2015

(65) Prior Publication Data

US 2015/0335843 A1 Nov. 26, 2015

(30) Foreign Application Priority Data

May 21, 2014 (JP) .................................. 2014-105147
May 30, 2014 (JP) .................................. 2014-112844
Jun. 12, 2014 (JP) .................................. 2014-121585

(51) Int. Cl.
*A62B 18/02* (2006.01)
*A61M 16/06* (2006.01)
*A61M 16/08* (2006.01)

(52) U.S. Cl.
CPC ........ *A61M 16/0683* (2013.01); *A61M 16/06* (2013.01); *A61M 16/0816* (2013.01); *A61M 2202/0208* (2013.01)

(58) Field of Classification Search
CPC .............. A61M 16/06; A61M 16/0605; A61M 16/0816; A61M 16/0875;
(Continued)

(56) References Cited

U.S. PATENT DOCUMENTS 2,248,477 A 7/1941 Lombard
2,535,938 A * 12/1950 Lombard .............. A61M 16/06
128/205.17
(Continued)

FOREIGN PATENT DOCUMENTS

JP S34-9100 B 10/1959
JP S6318154 U 2/1988
(Continued)

OTHER PUBLICATIONS

Office Action issued in JP Application No. 2014-105147 dated Apr. 20, 2017.
(Continued)

*Primary Examiner* — Joshua Lee
(74) *Attorney, Agent, or Firm* — Hunton Andrews Kurth LLP (57) ABSTRACT

A gas supply mask apparatus has low possibility that a gas rising in a mask main body will flow out from the upper end and the surrounding vicinity of the mask main body and give discomfort to the eyes of a mask wearer. In this gas supply mask apparatus, an angle formed between a direction in which a gas introduction opening faces and a virtual vertical plane facing right frontways falls within the range of 30° to 60° (preferably, the range of 35° to 55°, and more preferably, the range of 40° to 50°) when the mask main body is viewed right sideways.

20 Claims, 6 Drawing Sheets

(58) Field of Classification Search
CPC .......... A61M 2016/0661; A61M 16/08; A61M 16/0808; A61M 16/0825; A61M 16/0833; A61M 16/0841; A61M 16/085; A61M 16/0858; A61M 16/0866; A61M 16/0883; A61M 16/0891; A61M 2202/0208; A61M 16/0611; A61M 16/0616; A61M 16/0622; A61M 16/0627; A61M 16/0633; A61M 16/0638; A61M 16/0644; A61M 16/065; A61M 16/0655; A61M 16/0683; A61M 16/0688; A61M 16/0694; A61M 2016/0061; A62B 18/10; A62B 18/00; A62B 18/02; A62B 18/025; A62B 18/04; A62B 18/045; A62B 18/06; A62B 18/08; A62B 18/084; A62B 18/088

See application file for complete search history.

(56) References Cited

U.S. PATENT DOCUMENTS

| | | | |
|---|---|---|---|
| 2,928,387 A * | 3/1960 | Layne | A61M 16/0683 128/201.19 |
| 3,042,035 A * | 7/1962 | Coanda | A62B 18/00 128/206.24 |
| 3,680,555 A * | 8/1972 | Warncke | A62B 18/02 128/201.15 |
| 3,850,171 A | 11/1974 | Ball et al. | |
| 4,201,205 A * | 5/1980 | Bartholomew | A61M 16/06 128/205.25 |
| 4,279,037 A | 7/1981 | Morgan | |
| 4,794,921 A | 1/1989 | Lindkvist | |
| 4,875,477 A | 10/1989 | Waschke et al. | |
| 5,005,571 A | 4/1991 | Dietz | |
| 5,295,478 A * | 3/1994 | Baldwin | A61M 16/0048 128/202.28 |
| 5,441,046 A | 8/1995 | Starr et al. | |
| 5,465,712 A | 11/1995 | Malis et al. | |
| 5,483,953 A | 1/1996 | Cooper | |
| 5,724,965 A | 3/1998 | Handke et al. | |
| 5,738,094 A * | 4/1998 | Hoftman | A61M 16/06 128/206.24 |
| 6,035,852 A * | 3/2000 | Hoftman | A61M 16/06 128/206.21 |
| 6,491,034 B1 * | 12/2002 | Gunaratnam | A61M 16/06 128/202.27 |
| 6,675,796 B2 | 1/2004 | McDonald | |
| 7,926,487 B2 | 4/2011 | Drew et al. | |
| 8,042,540 B2 | 10/2011 | McDonald | |
| 8,646,449 B2 * | 2/2014 | Bowsher | A61M 16/06 128/201.28 |
| 8,733,356 B1 | 5/2014 | Roth | |
| 9,010,330 B2 | 4/2015 | Barlow et al. | |
| 9,144,656 B2 | 9/2015 | Lang et al. | |
| 9,186,474 B1 * | 11/2015 | Rollins, III | A61M 16/0605 |
| 9,272,108 B2 * | 3/2016 | Hu | A61M 16/06 |
| 9,901,697 B2 * | 2/2018 | Chien | A61M 16/0633 |
| 2003/0019495 A1 * | 1/2003 | Palkon | A61M 16/06 128/206.21 |
| 2003/0154984 A1 | 8/2003 | Fernandes | |
| 2004/0045550 A1 | 3/2004 | Lang et al. | |
| 2004/0112385 A1 | 6/2004 | Drew et al. | |
| 2006/0048774 A1 | 3/2006 | Townsend | |
| 2006/0081248 A1 * | 4/2006 | McDonald | A61M 16/06 128/205.25 |
| 2006/0102185 A1 * | 5/2006 | Drew | A61M 16/06 128/207.13 |
| 2006/0196510 A1 * | 9/2006 | McDonald | A61M 16/06 128/206.21 |
| 2007/0125379 A1 | 6/2007 | Pierro et al. | |
| 2007/0277828 A1 * | 12/2007 | Ho | A61M 16/08 128/206.21 |
| 2008/0149105 A1 | 6/2008 | Matula et al. | |
| 2009/0050156 A1 | 2/2009 | Ng et al. | |
| 2009/0250061 A1 * | 10/2009 | Marasigan | A61B 5/0836 128/205.13 |
| 2009/0260628 A1 * | 10/2009 | Flynn, Sr. | A61M 16/0078 128/203.28 |
| 2010/0122705 A1 | 5/2010 | Moenning | |
| 2010/0236549 A1 * | 9/2010 | Selvarajan | A61M 16/06 128/202.22 |
| 2010/0258133 A1 * | 10/2010 | Todd | A61M 15/009 128/207.12 |
| 2011/0155140 A1 | 6/2011 | Ho et al. | |
| 2011/0180078 A1 | 7/2011 | McKinley | |
| 2011/0197341 A1 | 8/2011 | Formica et al. | |
| 2011/0277770 A1 * | 11/2011 | Chang | A61M 16/06 128/206.21 |
| 2012/0042878 A1 | 2/2012 | Woo | |
| 2012/0055485 A1 | 3/2012 | Anthony | |
| 2012/0138061 A1 * | 6/2012 | Dravitzki | A61M 16/06 128/205.25 |
| 2012/0204872 A1 | 8/2012 | Cohen | |
| 2012/0222678 A1 | 9/2012 | Colbaugh | |
| 2012/0318271 A1 | 12/2012 | Ho | |
| 2012/0318274 A1 | 12/2012 | Ho | |
| 2013/0192601 A1 | 8/2013 | Reischl | |
| 2014/0090649 A1 | 4/2014 | Groll | |
| 2014/0107517 A1 | 4/2014 | Hussain | |
| 2014/0150798 A1 * | 6/2014 | Fong | A61M 16/06 128/206.21 |
| 2014/0305433 A1 * | 10/2014 | Rothermel | A61M 16/06 128/202.27 |
| 2014/0305436 A1 | 10/2014 | Nitta | |
| 2015/0107586 A1 * | 4/2015 | Kuo | A61M 16/0816 128/202.27 |
| 2015/0297854 A1 * | 10/2015 | McCracken | A61M 16/06 128/201.23 |
| 2015/0328423 A1 * | 11/2015 | Siew | A61M 16/06 128/205.25 |
| 2016/0008558 A1 * | 1/2016 | Huddart | A61M 16/06 128/205.25 |
| 2016/0184549 A1 * | 6/2016 | Bugamelli | A61M 16/0816 128/205.24 |
| 2016/0279370 A1 * | 9/2016 | McCracken | A61M 16/06 |
| 2016/0310688 A1 * | 10/2016 | Rothermel | A61M 16/0057 |

FOREIGN PATENT DOCUMENTS

| | | |
|---|---|---|
| JP | 2005-253925 | 9/2005 |
| WO | 2013144753 A1 | 10/2013 |

OTHER PUBLICATIONS

Office Action issued in JP Application No. 2014-121585 dated May 10, 2017.

Office Action issued in JP Application No. 2014-112844 dated May 12, 2017.

Non-Final Office Action dated Sep. 27, 2017, in U.S. Appl. No. 14/717,173.

Non-Final Office Action dated Sep. 28, 2017, in U.S. Appl. No. 14/717,180.

* cited by examiner

GAS SUPPLY MASK APPARATUS

CROSS-REFERENCE TO RELATED PATENT APPLICATIONS

This patent application claims priority to Japan Patent Application No. 2014-105147, filed May 21, 2014, and Japan Patent Application No. 2014-112844, filed May 30, 2014, and Japan Patent Application No. 2014-121585, filed Jun. 12, 2014, the disclosures of each of which are herein incorporated by reference in their entirety.

TECHNICAL FIELD

The present invention relates to a gas supply mask apparatus comprising a mask main body wearable on the head of a mask wearer, and a gas introduction opening capable of introducing a gas such as oxygen gas to a gas introduction space existing between a face of the mask wearer and the mask main body.

BACKGROUND

Figure 5:
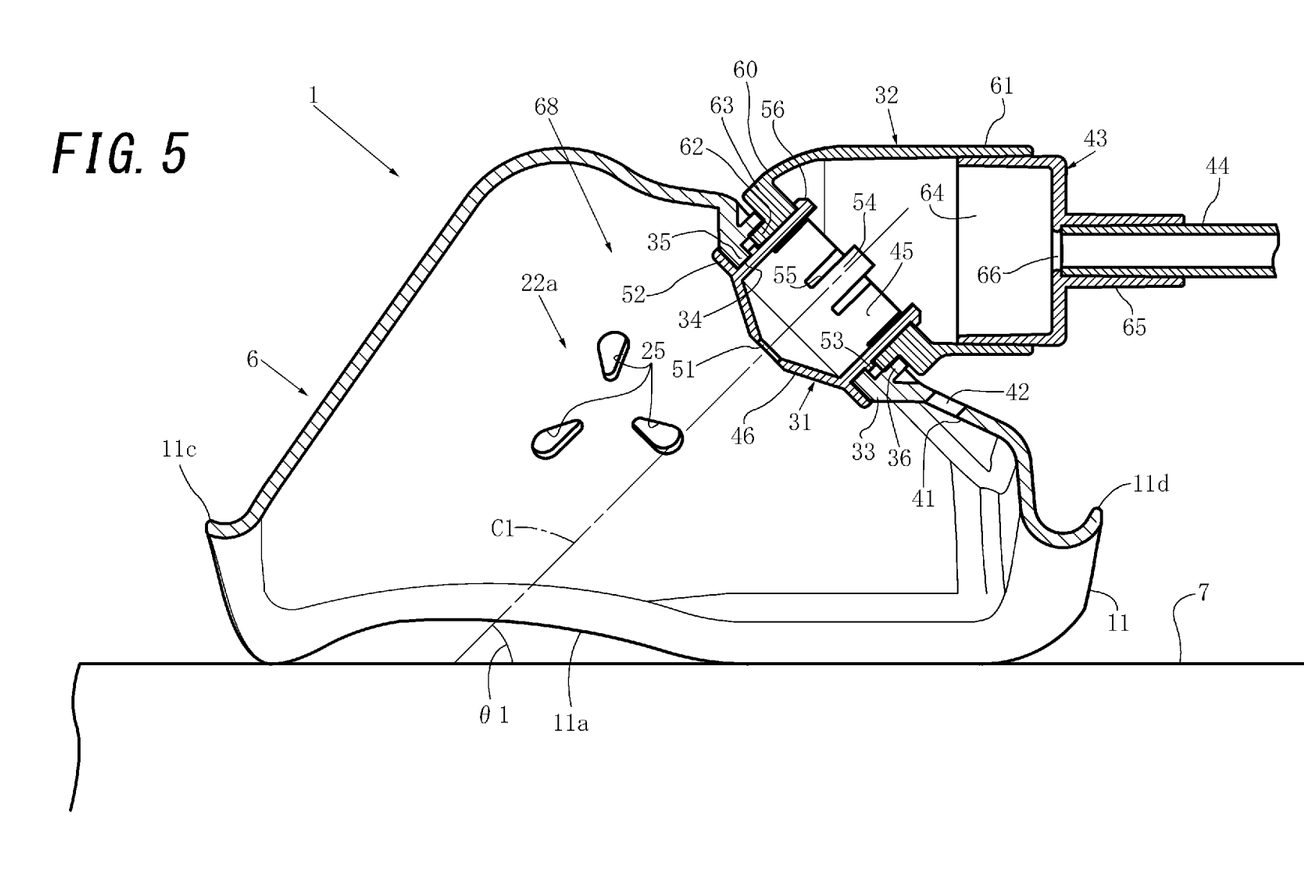
FIG. 5 is a longitudinal sectional view showing a state in which the oxygen mask apparatus shown in FIG. 1 is placed on a horizontal surface.
Figure 6:
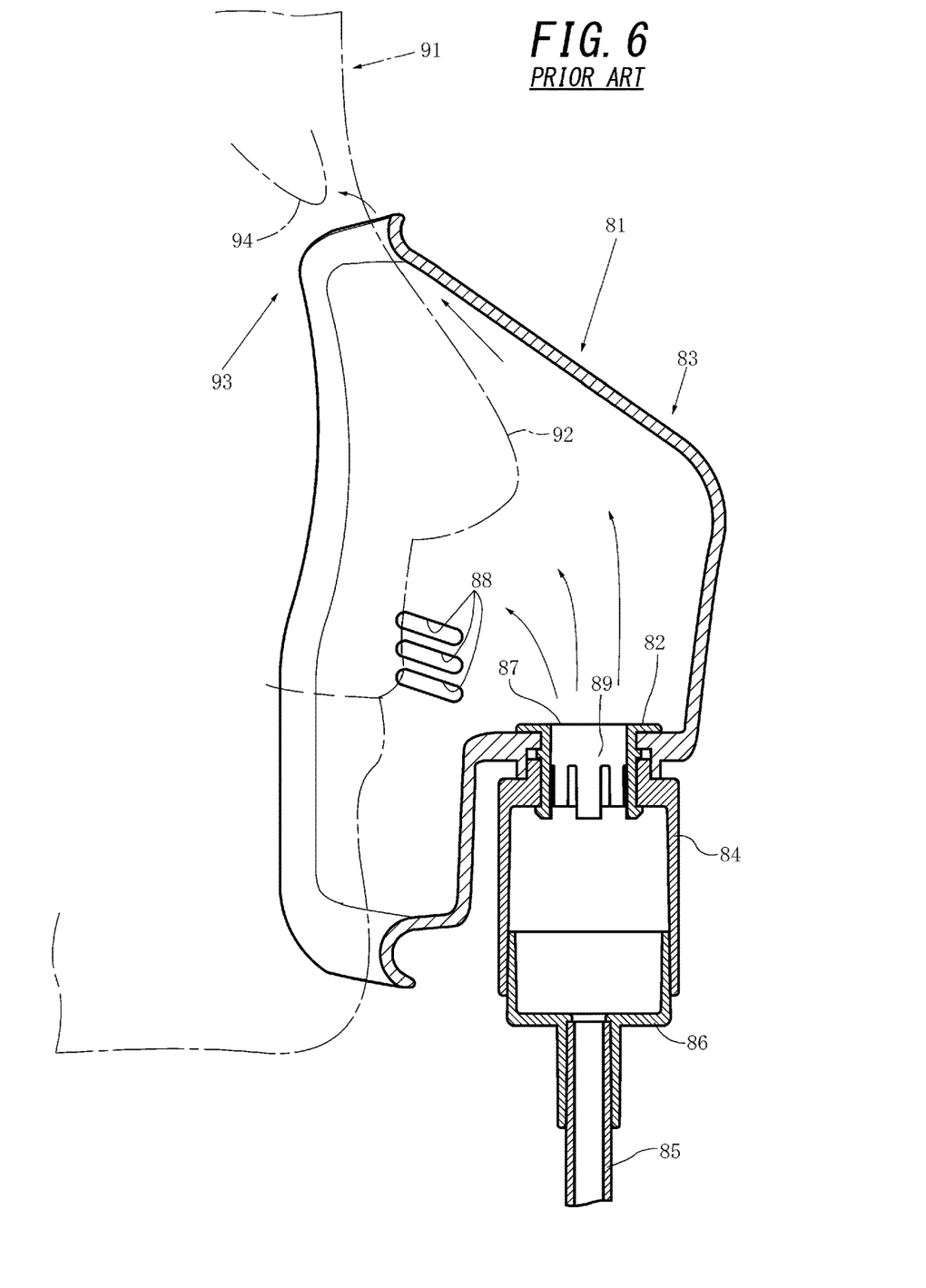
FIG. 6 is a longitudinal sectional view showing a state in which the conventional oxygen mask apparatus is in use.

In FIG. 6, a conventional oxygen mask apparatus is shown. A conventional oxygen mask apparatus 81 shown in FIG. 6 differs from an oxygen mask apparatus 1 according to an embodiment of the present invention shown in FIGS. 1 to 5 in points to be described below. That is, in the conventional oxygen mask apparatus 81, a first connector 82 is attached to a mask main body 83 such that the axis of the first connector 82 extends in a substantially vertical direction. In addition, a second connector 84 is formed into a substantially cylindrical shape so that the axis of the second connector 84 extends in a substantially vertical direction. Therefore, oxygen gas which rises substantially vertically from a gas supply tube 85 rises substantially vertically in a third connector 86, and is introduced to the second connector 84. Also, this oxygen gas introduced to the second connector 84 rises in the first connector 82. Accordingly, the oxygen gas rises in the mask main body 83 while diffusing from a relatively large upper-end opening 87 of the first connector 82. Therefore, a mask wearer 91 can relatively easily inhale, from the nostrils, the oxygen gas flowing to an area, below a nose 92, and the surrounding vicinity. Reference numeral 88 denotes three holes in the oxygen mask.

In the conventional oxygen mask apparatus 81, however, the upper-end opening 87 of the first connector 82 has substantially the same diameter as that of an inner circumferential hole (in other words, a through hole) 89 of the first connector 82. Accordingly, the oxygen gas flowing into the mask main body 83 from the upper-end opening 87 may evenly spread to substantially the whole interior of the mask main body 83. To allow the mask wearer 91 to properly inhale the oxygen gas from the nostrils, therefore, a relatively large amount of the oxygen gas must be supplied into the mask main body 83. Accordingly, if the mask main body 83 is not well fitted on a face 93 of the mask wearer 91, the oxygen gas having risen in the mask main body 83 may flow out from the upper end and the surrounding vicinity of the mask main body 83, and flow toward an eye 94 of the mask wearer 91. As a consequence, the eye 94 of the mask wearer 91 may become dry, and the mask wearer 91 may have discomfort on the eye 94.

SUMMARY OF THE INVENTION

The present invention can effectively correct the above-described drawback of the conventional oxygen mask apparatus 81 by using a relatively simple arrangement.

According to the first aspect, the present invention is directed to a gas supply mask apparatus comprising a mask main body wearable on a head of a mask wearer, and a gas introduction opening capable of introducing a gas to a gas introduction space existing between a face of the mask wearer and the mask main body, wherein in a mask placement state in which the mask main body is placed upward on a horizontal surface, a first angle formed between the horizontal surface and a direction in which said gas introduction opening faces falls within a range of 30° to 60° (preferably, a range of 35° to 55°, and more preferably, a range of 40° to 50°) when said mask main body is viewed from the side. According to the first mode of the first aspect of the present invention, in the above-mentioned mask placement state, a second angle formed between the direction in which said gas introduction opening faces and a bisecting central line which bisects said mask main body into left and right halves when the mask main body is viewed from above falls within a range of 0° to 15° (preferably, a range of 0° to 10°, and more preferably, a range of 0° to 5°) when the mask main body is viewed from above.

According to the second aspect, the present invention is directed to a gas supply mask apparatus comprising a mask main body wearable on a head of a mask wearer, and a gas introduction opening capable of introducing a gas to a gas introduction space existing between a face of the mask wearer and said mask main body, wherein in a correct mask wearing state in which a mask wearer having an average body shape and an average head shape is correctly wearing the mask main body and facing right forward, a third angle formed between a direction in which said gas introduction opening faces and a virtual vertical plane facing right forward falls within a range of 30° to 60° (preferably, a range of 35° to 55°, and more preferably, a range of 40° to 50°) when said mask main body is viewed from the side. According to the first mode of the second aspect of the present invention, in the above-mentioned correct mask wearing state, a fourth angle formed between the direction in which said gas introduction opening faces and a bisecting central line which bisects said mask main body into left and right halves when said mask main body is viewed from the front falls within a range of 0° to 15° (preferably, a range of 0° to 10°, and more preferably, a range of 0° to 5°) when said mask main body is viewed from the front.

According to each of the second mode of the first aspect and the second mode of the second aspect of the present invention, the apparatus further comprises a gas supply cylindrical portion configured to supply said gas into the mask main body from outside said mask main body through said gas introduction opening, wherein said gas supply cylindrical portion comprises a first cylindrical portion configured to transfer said gas substantially upward, and a second cylindrical portion connected to said first cylindrical portion, and said second cylindrical portion is configured to supply said gas to said gas instruction opening after deflecting a direction of a flow of said gas supplied from said first cylindrical portion to the direction in which said gas introduction opening faces.

According to each of the third mode of the first aspect and the third mode of the second aspect of the present invention, the apparatus further comprises a first connector including said gas introduction opening, and a second connector connected to said first connector to extend outside said mask main body, wherein said second connector includes an upper cylindrical portion integrated with a lower cylindrical portion extending substantially downward, such that said upper cylindrical portion extends obliquely upward in a bent state from said lower cylindrical portion, and said upper cylindrical portion is configured to be pivotal with respect to said first connector.

According to each of the fourth mode of the first aspect and the fourth mode of the second aspect of the present invention, said first connector includes a cylindrical portion extending substantially along the direction in which said gas introduction opening faces, an upper-end surface portion having a substantially pyramidal shape such as a substantially conical shape and formed on an upper-end side of said cylindrical portion such that said upper-end surface portion having substantially pyramidal shape such as a substantially conical shape projects toward the upper-end side, and said gas introduction opening formed in a substantially central portion of said substantially pyramidal upper-end surface portion having a substantially pyramidal shape such as a substantially conical shape. According to the first practical mode of the fourth mode of each of the first and second aspects, a length of the cylindrical portion of the first connector in the axial direction falls within a range of 12 to 24 mm (more preferably, a range of 13.5 to 22.5 mm, and most preferably, a range of 14.5 to 21.5 mm), an inside area of the cylindrical portion of the first connector in a direction substantially perpendicular to the axial direction falls within a range of 140 to 290 $mm^2$ (more preferably, a range of 165 to 275 $mm^2$, and most preferably, a range of 175 to 265 $mm^2$), and an opening area of said gas introduction opening falls within a range of 4.8 to 9.2 $mm^2$ (more preferably, a range of 5.2 to 8.8 $mm^2$, and most preferably, a range of 5.6 to 8.4 $mm^2$). In this case, according to the second practical mode of the fourth mode of each of the first and second aspects, said cylindrical portion of said first connector has a substantially circular cylindrical shape, an inner diameter of said cylindrical portion of said first connector falls within a range of 10 to 20 mm (more preferably, a range of 11.5 to 18.5 mm, and most preferably, a range of 12.5 to 17.5 mm), said gas introduction opening has a substantially circular shape, and a diameter of said gas introduction opening falls within a range of 2 to 4 mm (more preferably, a range of 2.2 to 3.8 mm, and most preferably, a range of 2.4 to 3.6 mm). Furthermore, according to each of the fifth mode of the first aspect and the fifth mode of the second aspect of the present invention, the above-mentioned gas supply mask apparatus is an oxygen mask apparatus.

According to each of the first and second aspects of the present invention, regardless of whether or not said mask main body is well fitted on the face of the mask wearer, the possibility that a gas rising in said mask main body will flow out from the upper end and the surrounding vicinity of said mask main body and flow toward the eyes of the mask wearer is not high. Therefore, the possibility that said gas will flow to the eyes of the mask wearer, dry the eyes of the mask wearer, and give the mask wearer discomfort on his or her eyes, is low. In this case, the possibility that the mask wearer will have discomfort on his or her eyes decreases more according to the above-mentioned preferable numerical range (in other words, the range of 35° to 55°). In addition, the possibility that the mask wearer will have discomfort on his or her eyes further decreases in the above-mentioned more preferable numerical range (in other words, the range of 40° to 50°).

According to each of the first mode of the first aspect and the first mode of the second aspect of the present invention, the mask wearer can relatively reliably inhale a gas from the nostrils. In this case, the mask wearer can more reliably inhale a gas in the above-mentioned preferable range (in other words, the range of 0° to 10°). In addition, the mask wearer can further reliably inhale a gas in the above-mentioned more preferable range (in other words, the range of 0° to 5°).

According to each of the second mode of the first aspect and the second mode of the second aspect of the present invention, when supplying a gas from said gas supply tube to said gas introduction opening through said gas supply cylindrical portion, said gas supply tube can be suspended substantially below from said gas supply cylindrical portion. This makes handling of said gas supply tube relatively easy as in the conventional oxygen mask apparatus. According to each of the third mode of the first aspect and the third mode of the second aspect of the present invention, the effect achieved by each of the second mode of the first aspect and the second mode of the second aspect of the present invention can be achieved more reliably with a relatively reliable operation and relatively simple structure.

According to each of the fourth mode of the first aspect and the fourth mode of the second aspect of the present invention, a gas supplied inside said mask main body through said gas introduction opening can be supplied relatively reliably to the nostrils, and their immediate vicinity, of the mask wearer. According to each of the first and second practical modes of each of the fourth mode of the first aspect and the fourth mode of the second aspect of the present invention, the effect achieved by each of the fourth mode of the first aspect and the fourth mode of the second aspect of the present invention can be achieved more reliably with a relatively reliable operation and relatively simple structure. Furthermore, according to each of the fifth mode of the first aspect and the fifth mode of the second aspect of the present invention, it is possible to provide an oxygen mask apparatus capable of achieving the above-described effects achieved by each of the above-mentioned first and second aspects.

According to another exemplary embodiment, a gas mask supply connecting apparatus that connects a gas supply tube to a gas mask is disclosed, which comprises a first connector having a first gas opening through which a gas exits the first connector and enters the gas mask in a first direction that corresponds to an axial direction of the first connector, such that the gas traveling in the first direction upon exiting the first connector travels linearly to a location immediately below nostrils of a wearer of the gas mask; and the gas supply tube connects to the first connector, wherein the gas exits the gas supply tube in a second direction parallel to a planar surface corresponding to a surface of the wearer of the gas mask, such that the first connector causes a flow direction of the gas to change from the second direction to the first direction.

The above, and other, objects, features and advantages of this invention will become readily apparent from the following detailed description thereof which is to be read in connection with the accompanying drawings.

DETAILED DESCRIPTION

Next, an oxygen mask apparatus according to an embodiment of the present invention will be explained with reference to FIGS. 1 to 5 by dividing the explanation into "1. Explanation of Oxygen Mask Main Body", "2. Explanation of First to Fourth Connectors and Gas Supply Tube", and "3. Explanation of Direction in Which Gas Is Blown to Mask Main Body".

1. Explanation of Oxygen Mask Main Body

Figure 2:
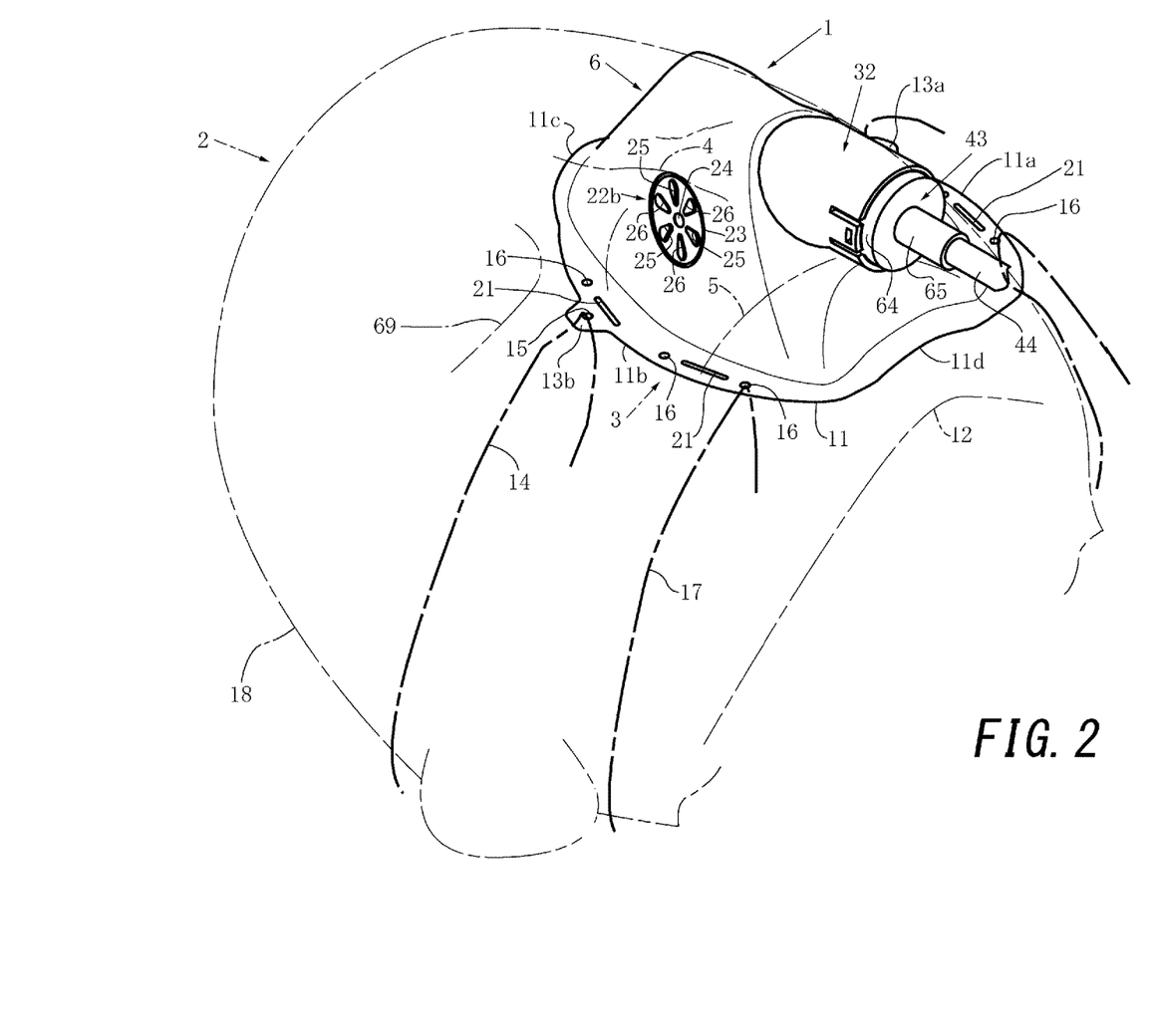
FIG. 2 is a perspective view showing the state in which the oxygen mask apparatus shown in FIG. 1 is in use.

As shown in FIGS. 2 and 5, an oxygen mask apparatus 1 as a gas supply mask apparatus includes a mask main body 6 capable of covering a substantially central portion (more specifically, a nose 4 and a mouth 5 and their peripheries) of a face 3 of a mask wearer 2 such as a patient. Note that the mask main body 6 can integrally be molded from a substantially transparent (in other words, light-transmitting) soft synthetic resin such as soft vinyl chloride so as to have a substantially bisymmetrical shape and substantially bisymmetrical pattern. At least left and right side portions 11a and 11b of an outer peripheral portion 11 of the mask main body 6 are so formed as to form a substantially flat surface over a substantially whole region (in other words, a substantially horizontal surface is formed when the mask main body 6 is placed upward on a horizontal surface 7 as shown in FIG. 5). Note that an upper side portion 11c of the outer peripheral portion 11 has a curved shape which slightly projects forward (in other words, outward), so as to substantially fit the shape of the nose 4 of the mask wearer 2. A lower side portion 11d of the outer peripheral portion 11 forms a substantially flat surface which substantially continues to the left and right side portions 11a and 11b, so as to substantially fit a portion (and the vicinity) above a chin 12 of the mask wearer 2. However, the lower side portion 11d may also have a curved shape which slightly projects forward (in other words, outward), so as to substantially fit a portion (and the vicinity) below the chin 12 of the mask wearer 2.

Figure 3:
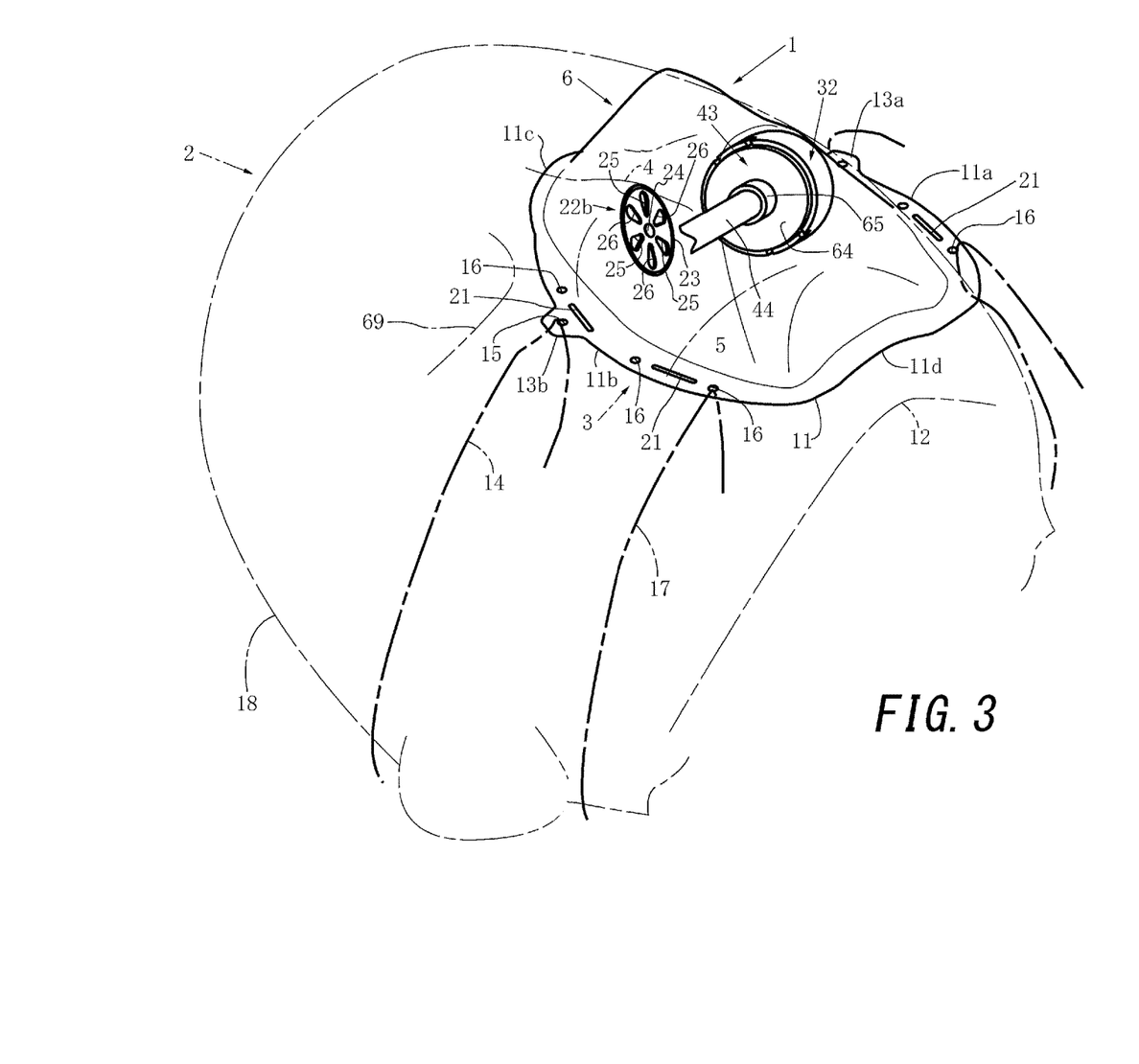
FIG. 3 is a perspective view similar to FIG. 2, in a state in which an oxygen supply tube is pivoted to the right.

As shown in, e.g., FIG. 3, in slightly upper portions of middle portions of the pair of left and right side portions 11a and 11b of the outer peripheral portion 11 of the mask main body 6, left and right projections 13a and 13b which project into a substantially trapezoidal shape from the pair of left and right side portions 11a and 11b toward the left and right sides are formed. A pair of left and right insertion holes 15 are formed in the left and right projections 13a and 13b. The left and right end portions of a flat elastic string 14 as a flexible longitudinal attaching member are inserted into and attached to the insertion holes 15. Also, similar insertion holes 16 are arranged along a substantially longitudinal direction of each of the pair of left and right side portions 11a and 11b, and the number of insertion holes 16 is, e.g., three. Furthermore, each of the two ends of a second elastic string 17 which can be formed like the elastic string 14 may be inserted into and attached to one of the three insertion holes 16, in place of or in addition to the elastic string 14. A pair of upper and lower insertion slits 21 are formed in each of the pair of left and right side portions 11a and 11b. The upper one of the pair of upper and lower insertion slits 21 is adjacent to the insertion hole 15 (in other words, the projection 13a or 13b) in a substantially horizontal direction. Note that the two end portions of an elastic bandage as a flexible longitudinal attaching member can be inserted into and attached to a pair of left and right insertion slits of the insertion slits 21, instead of the flat elastic string 14. Also, each of the elastic strings 14 and 17 and elastic bandage is extended over a head (in other words, a head including the face of a person) 18 of the mask wearer 2, so as to pass through the left cheek, the back of the head, and the right cheek of the mask wearer 2.

Figure 1:
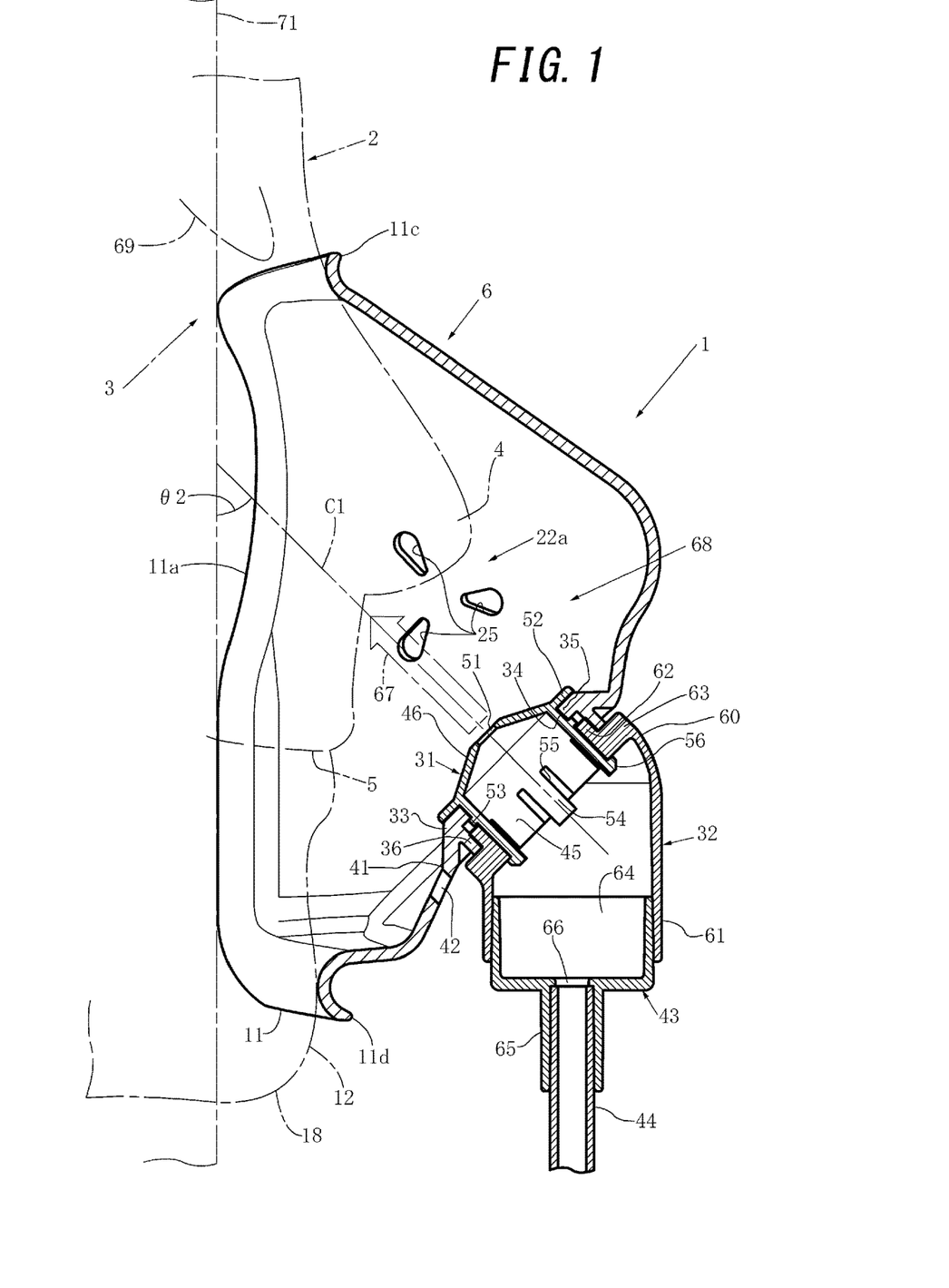
FIG. 1 is a longitudinal sectional view showing an embodiment in which the present invention is applied to an oxygen mask apparatus, in a state in which the oxygen mask apparatus is in use.

As shown in, e.g., FIGS. 1 and 2, in slightly upper portions of the left and right sides of the mask main body 6, a pair of left and right hole pattern portions 22a and 22b for communicating the inside and outside of the mask main body 6 are formed into flower patterns. Note that when the mask main body 6 is worn on the mask wearer 2, the pair of left and right hole pattern portions 22a and 22b are arranged in positions relatively close to the left and right nostrils of the mask wearer 2. The right hole pattern portion 22b can have substantially the same bisymmetrical shape and bisymmetrical pattern as those of the left hole pattern portion 22a. In the following description, therefore, the right hole pattern portion 22b will be explained in detail, and a detailed explanation of the left hole pattern portion 22a will be omitted.

As shown in, e.g., FIGS. 1 and 2, the hole pattern portion 22b has an outer peripheral projection 23 which projects substantially outward when viewed from outside the mask main body 6 and has a substantially circular shape. A central projection (in other words, a flower stem) 24 which projects substantially outward when viewed from outside the mask main body 6 is formed at a substantially center of the outer peripheral projection 23. Also, a plurality of (in the embodiment shown in the drawings, six) petals extending substantially radially from the central projection 24 to the outer peripheral projection 23 are formed between the outer peripheral projection 23 and central projection 24. Note that the plurality of petals includes a plurality of (in the embodiment shown in the drawings, three) first petals 25 formed by through holes, and a plurality of (in the embodiment shown in the drawings, three) second petals 26 formed by recesses which face the outside between the first petals 25. The plurality of petals 25 and 26 (in other words, the plurality of first petals 25 and the plurality of second petals 26) are sequentially arranged at substantially equal angles along the outer periphery of the flower stem 24. As shown in, e.g., FIGS. 1 and 5, the plurality of (in the embodiment shown in the drawings, three) first petals 25 are arranged on the inner circumferential surface of the mask main body 6 at substantially equal angles (in the embodiment shown in the drawings, an interval of 60°).

As shown in, e.g., FIGS. 1 and 5, in a portion slightly below a substantially central portion of the mask main body 6, a connector attaching portion 33 for attaching first and second connectors 31 and 32 is formed. Note that the connector attaching portion 33 includes a hole 34 having a substantially pillar shape such as a substantially circular pillar shape, a substantially ring-like projecting wall 35 which projects toward the hole 34 so as to form the outer periphery of the hole 34, and a projecting wall portion 36 which projects outward from the outer periphery and the vicinity of the projecting wall 35 and has a substantially cylindrical shape such as a substantially circular cylindrical shape. Also, the connector attaching portion 33 (in other words, the ring-like projecting wall 35 and cylindrical projecting wall portion 36) is formed in the mask main body 6 so as to incline to the horizontal direction and vertical direction of the mask main body 6 in FIG. 5. This inclination direction of the connector attaching portion 33 in FIG. 5 can be a direction in which the connector attaching portion 33 projects outward from below. In addition, in a substantially lower portion of the connector attaching portion 33 in FIG. 5, a second connector attaching portion 41 capable of connecting a gas concentration measurement tube (not shown) is formed adjacent to the connector attaching portion 33. The second connector attaching portion 41 has a hole 42 such as a substantially circular hole. Furthermore, the second connector attaching portion 41 (in other words, the hole 42) is slightly inclined to the vertical direction in FIG. 5. This inclination direction of the second connector attaching portion 41 can be a direction in which the second connector attaching portion 41 slightly projects outward from below. Note that the above-mentioned gas concentration measurement tube can be used to measure the concentration of a gas such as carbon dioxide in the interior of the mask main body 6.

2. Explanation of First to Fourth Connectors and Oxygen Supply Tube

As shown in, e.g., FIGS. 1 and 5, the oxygen mask apparatus 1 includes the first connector 31, the second connector 32, a third connector 43, a gas supply tube 44, and a fourth connector (not shown). Note that each of the first to fourth connectors can integrally be molded from a substantially transparent (in other words, light-transmitting) hard synthetic resin such as hard vinyl chloride. Note also that the gas supply tube 44 can integrally be molded from a substantially transparent (in other words, light-transmitting) soft synthetic resin such as soft vinyl chloride. The first connector 31 includes a gas supply cylindrical portion 45 which extends along substantially an axial direction C1 of the first connector 31 and has a cylindrical shape such as a substantially circular cylindrical shape, and an upper-end surface portion 46 which is formed on the upper-end side of the cylindrical portion 45 so as to project toward the upper-end side, and has a pyramidal shape such as a substantially conical shape. Also, a substantially circular opening 51 for introducing oxygen (in other words, for introducing a gas to the inside of the mask main body 6) is formed in a substantially central portion of the substantially pyramidal upper-end surface portion 46. In addition, a substantially ring-like outward flange 52 projecting in a direction substantially perpendicular to the axial direction C1 is formed on the outer periphery of the upper-end surface portion 46. Furthermore, a substantially ring-like second outer flange 53 projecting in a direction substantially perpendicular to the axial direction C1 is formed on the outer periphery of the cylindrical portion 45, which is outside the outward flange 52. Note that the second outward flange 53 can have substantially the same inner diameter as that of the outward flange 52, and an outer diameter much smaller than that of the outward flange 52. The cylindrical portion 45 has four engaging claws 54 formed at preferably substantially equal angular intervals (in other words, intervals of substantially 90°) along the circumferential direction. Therefore, slits (in other words, notches) 55 extending from the lower end to a middle portion in the axial direction are formed on the two sides of each of the four engaging claws 54 of the cylindrical portion 45. An engaging projection 56 projects from the outer surface of the lower end portion of each engaging claw 54. Note that in each engaging claw 54, only the engaging projection 56 projects downward in the axial direction C1 when compared to other portions of the cylindrical portion 45 except the engaging claw 54. When attaching the first connector 31 to the mask main body 6, the cylindrical portion 45 of the first connector 31 is inserted into the opening 34 from inside the mask main body 6. Note that by this insertion, the second outward flange 53 climbs over the ring-like projecting wall 35 of the mask main body 6 due to elastic deformation of the mask main body 6 and the like. Consequently, the ring-like projecting wall 35 of the mask main body 6 is clamped between the outward flange 52 of the first connector 31 and the second outward flange 53 of the first connector 31, so the first connector 31 is attached to the mask main body 6.

In the embodiment shown in the drawings, the cylindrical portion 45 having a substantially cylindrical shape such as a substantially circular cylindrical shape of the first connector 31 shown in, e.g., FIGS. 1 and 5 has an inner diameter of approximately 15 mm, a length of approximately 18 mm in the axial direction C1, and an inside area of approximately 220 $mm^2$ in a direction substantially perpendicular to the axial direction C1. Also, in the embodiment shown in the drawings, the gas introduction opening 51 of the first connector 31 has a diameter of approximately 3 mm, and an opening area of approximately 7 $mm^2$, which indicates the size of the opening 51. The numerical values of these portions of the first connector 31 generally preferably fall within ranges described in items (a) to (e) below from the viewpoint of practicality:

(a) the inner diameter of the cylindrical portion 45 having a substantially cylindrical shape such as a substantially circular cylindrical shape: the range of 10 to 20 mm (more preferably, the range of 11.5 to 18.5 mm, and most preferably, the range of 12.5 to 17.5 mm), (b) the length of the cylindrical portion 45 having a substantially cylindrical shape such as a substantially circular cylindrical shape in the axial direction C1: the range of 12 to 24 mm (more preferably, the range of 13.5 to 22.5 mm, and most preferably, the range of 14.5 to 21.5 mm), (c) the inside area of the cylindrical portion 45 having a substantially cylindrical shape such as a substantially circular cylindrical shape in the direction substantially perpendicular to the axial direction C1: the range of 140 to 290 $mm^2$ (more preferably, the range of 165 to 275 $mm^2$, and most preferably, the range of 175 to 265 $mm^2$), (d) the diameter of the gas introduction opening 51: the range of 2 to 4 mm (more preferably, the range of 2.2 to 3.8 mm, and most preferably, the range of 2.4 to 3.6 mm), and (e) the opening area of the gas introduction opening 51: the range of 4.8 to 9.2 $mm^2$ (more preferably, the range of 5.2 to 8.8 $mm^2$, and most preferably, the range of 5.6 to 8.4 $mm^2$).

As shown in, e.g., FIGS. 1 and 5, a portion 61 on the lower-end side of the second connector 32 forms a lower cylindrical portion having a substantially cylindrical shape such as a substantially circular cylindrical shape to which the third connector 43 is attached. Note that in the state shown in FIG. 1, the lower cylindrical portion 61 extends in a substantially vertical direction. A portion 60 on the upper-end side of the second connector 32 forms an upper cylindrical portion being obliquely bent upward from the portion 61 on the lower-end side of the second connector 32, so as to extend along substantially the axial direction C1. An upper-end portion 62 having a substantially cylindrical shape such as a substantially circular cylindrical shape of the second connector 32 is inserted between the cylindrical portion 45 of the first connector 31 and the cylindrical projecting wall 36 of the mask main body 6. By this insertion, a ring-like upper wall 63 of the second connector 32 abuts against the lower end of the cylindrical projecting wall 36 of the mask main body 6. Also, the engaging projections 56 of the engaging claws 54 of the first connector 31 engage with the lower surface of the ring-like upper wall 63 in order to prevent removal. As a consequence, the second connector 32 is attached to the first connector 31 in a state in which the second connector 32 relatively easily pivots with respect to the first connector 31. In addition, as shown in, e.g., FIGS. 1 and 2, the third connector 43 includes a large-diameter, closed-end cylindrical portion 64 having a circular cylindrical shape or the like, and a small-diameter cylindrical portion 65 having a circular cylindrical shape and connected to the lower end portion of the cylindrical portion 64 by integral molding or the like. Note that a through hole 66 for communicating with the cylindrical portion 65 is formed in a substantially central position of the bottom of the cylindrical portion 64. One end portion of the gas supply tube 44 is inserted into and connected to the small-diameter cylindrical portion 65. Also, the upper-end opening of the gas supply tube 44 communicates with the large-diameter cylindrical portion 64 through the through hole 66. Furthermore, the above-mentioned fourth connector (not shown) is connected to the other end portion of the gas supply tube 44. The fourth connector can be connected to a gas cylinder (not shown) such as an oxygen cylinder or to a gas supply nozzle (not shown) installed in a hospital room as needed.

3. Explanation of Direction in which Gas is Blown to Mask Main Body

Regardless of whether or not the oxygen mask apparatus 1 is worn on the face 3 of the mask wearer 2 as shown in, e.g., FIG. 1, the direction of a gas flow 67 (in other words, the direction in which the gas introduction opening 51 points) supplied from the first connector 31 to the internal space 68 of the mask main body 6 (in other words, a gas introduction space existing between the face 3 and mask main body 6) substantially matches the axial direction C1. When the oxygen mask apparatus 1 (in other words, the mask main body 6) is placed upward on the horizontal surface 7 as shown in FIG. 5 (this state will be referred to as "the mask placement state shown in FIG. 5" hereinafter), the axial direction C1 extends in a substantially vertical direction of the mask main body 6 (in other words, the oxygen mask apparatus 1) in a planar view. In a planar view, therefore, the axial direction C1 substantially matches a virtual bisecting central line (in other words, a central line extending in the vertical direction of the mask main body 6) which bisects the mask main body 6 (in other words, the oxygen mask apparatus 1) shown in FIG. 5 into left and right halves when viewed from just above, so the angle formed between them is substantially 0° in a planar view. Also, in the mask placement state shown in FIG. 5, the axial direction C1 linearly extends in oblique direction from a substantially lower portion of the front surface portion of the mask main body 6 (in other words, the oxygen mask apparatus 1) to a substantially upper portion of the rear surface portion of the mask main body 6. An angle θ1 formed between the axial direction C1 and horizontal surface 7 is substantially 45° when the mask main body 6 is viewed sideways (in other words, in the mask placement state shown in FIG. 5). Furthermore, FIG. 1 shows a mask wearing state (to be referred to as "the correct mask wearing state shown in FIG. 1" hereinafter) in which a person (in other words, the mask wearer 2) having an average body shape and average head shape is correctly wearing the oxygen mask apparatus 1 (in other words, the mask main body 6) and facing right forward. Note that when compared to the state in which the oxygen mask apparatus 1 is placed upward on the horizontal surface 7 as shown in FIG. 5, the substantially only difference of this correct mask wearing state shown in FIG. 1 is that the oxygen mask apparatus 1 is raised substantially 90°. Accordingly, the horizontal surface 7 in FIG. 5 is replaced with a virtual perpendicular plane 71 (in other words, a virtual vertical plane) in FIG. 1. Also, the angle θ1 in FIG. 5 is replaced with an angle θ2 in FIG. 1. Note that in order to achieve the object of the present invention, each of the angles θ1 and θ2 generally preferably falls within the range of 30° to 60°, more preferably, the range of 35° to 55°, and most preferably, the range of 40° to 50°, from the viewpoint of practicality. In addition, in order to achieve the object of the present invention, an angle θ3 (not shown) which the axial direction C1 makes with a virtual bisecting central line (in other words, a bisecting central line extending from the head side to the chin side of the mask main body 6) which bisects the mask main body 6 (in other words, the oxygen mask apparatus 1) into left and right halves when the mask main body 6 is viewed frontways generally preferably falls within the range of 0° to 15°, more preferably, the range of 0° to 10°, and most preferably, the range of 0° to 5°, from the viewpoint of practicality.

When a gas such as oxygen gas is supplied to the above-mentioned fourth connector in the mask wearing state in which the mask wearer 2 is wearing the oxygen mask apparatus 1 as shown in FIG. 1, this gas is supplied from the fourth connector to the second connector 32 through the gas supply tube 44 and third connector 43. The gas supplied to the second connector 32 is supplied from the second connector 32 to the inside of the mask main body 6 through the oxygen introduction opening 51 (in other words, the gas introduction opening 51 of the mask main body 6) of the first connector 31. Note that the above-mentioned gas supply direction in the mask main body 6 substantially matches the direction in which the gas flow 67 is blown to the inside of the mask main body 6 (in other words, the direction in which the gas introduction opening 51 faces), so the gas is supplied to a portion slightly or immediately below the nostrils and the vicinities under the nose 4 of the mask wearer 2. Accordingly, the mask wearer 2 can inhale the gas extremely easily and extremely reliably. Also, an extra gas existing between the mask wearer 2 and mask main body 6 can be released, as needed, outside the mask main body 6 by a natural flow through the three first petals (in other words, the holes) 25. Therefore, the possibility that the gas will flow to an eye 69 of the mask wearer 2 and give the mask wearer 2 discomfort is not so high.

Figure 4:
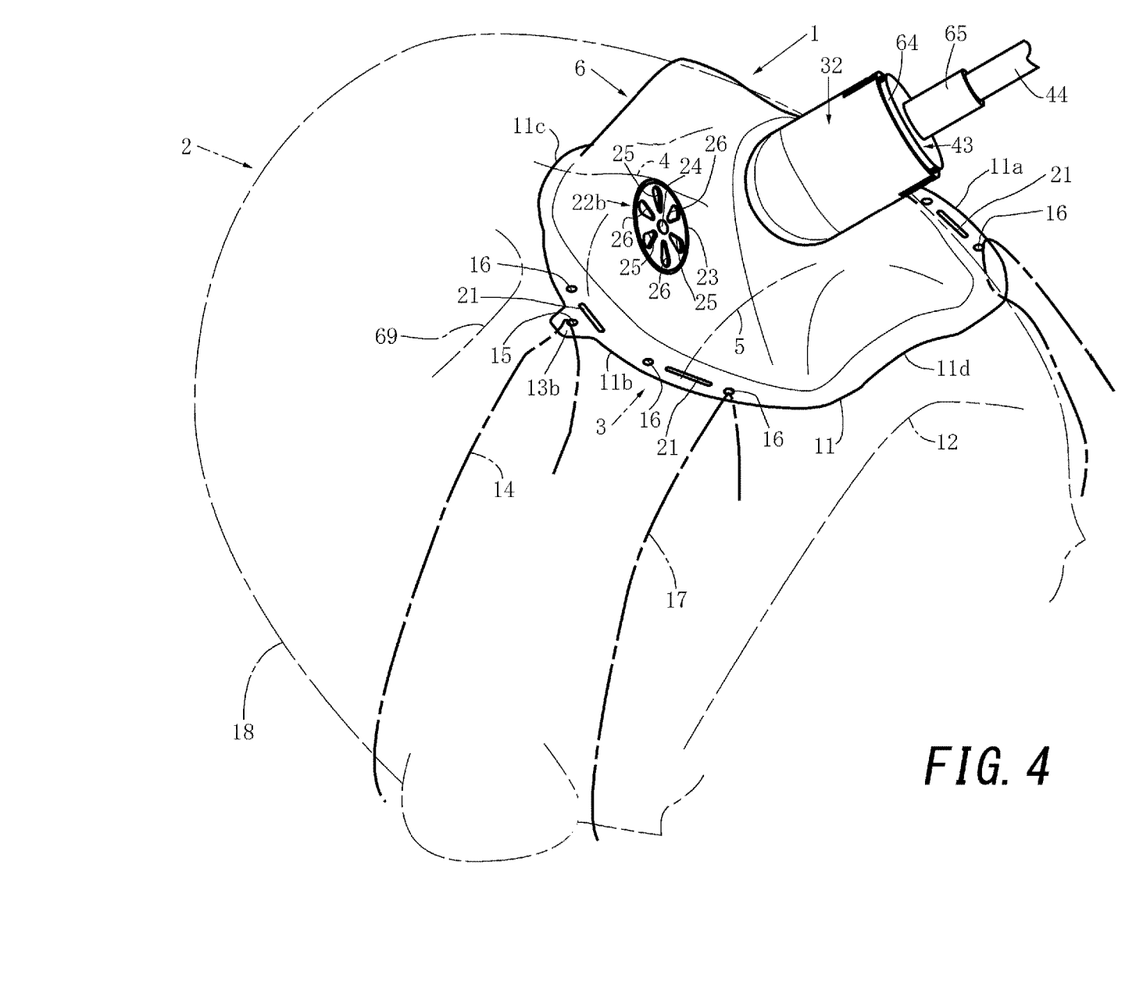
FIG. 4 is a perspective view similar to FIG. 2, in a state in which the oxygen supply tube is pivoted to the left.

When the gas supply tube 44 is not shifted to the left or right as shown in FIG. 2 when viewed frontways, the second connector 32 is positioned substantially just below the lower end of the first connector 31 as shown in, e.g., FIGS. 1 and 2. However, when the gas supply tube 44 moves forward to the right side of the mask main body 6 as shown in FIG. 3 from the state shown in FIG. 2 for some reason, the second connector 32 pivots forward clockwise in FIG. 2 with respect to the first connector 31 (in other words, the mask main body 6). Even in a case like this, therefore, the gas supply tube 44 is not particularly twisted or bent, and holds a substantially normal gas supply state. When the gas supply tube 44 moves backward from the state shown in FIG. 3 to the state shown in FIG. 2, the second connector 32 pivots backward counterclockwise in FIG. 3 with respect to the first connector 31 (in other words, the mask main body 6). Even in a case like this, therefore, the gas supply tube 44 is not particularly twisted or bent, and holds a substantially normal gas supply state. Furthermore, when the gas supply tube 44 moves forward to the left side of the mask main body 6 as shown in FIG. 4 from the state shown in FIG. 2 for some reason, the second connector 32 pivots forward counter-clockwise in FIG. 2 with respect to the first connector 31 (in other words, the mask main body 6). Even in a case like this, therefore, the gas supply tube 44 is not particularly twisted or bent, and holds a substantially normal gas supply state. When the gas supply tube 44 moves backward from the state shown in FIG. 4 to the state shown in FIG. 2, the second connector 32 pivots backward clockwise in FIG. 3 with respect to the first connector 31 (in other words, the mask main body 6). Even in a case like this, therefore, the gas supply tube 44 is not particularly twisted or bent, and holds a substantially normal gas supply state.

Having described a specific preferred embodiment of the present invention with reference to the accompanying drawings, it is to be understood that the invention is not limited to these precise embodiments, and that various changes and modifications may be effected therein by one skilled in the art without departing from the scope or spirit of the invention as defined in the appended claims.

For example, the first connector 31 and second connector 32 are separate in the above-described embodiment. However, the first connector 31 and second connector 32 can also be integrated.

In addition, the third connector 43 and second connector 32 are separate in the above-described embodiment. However, the third connector 43 and second connector 32 can also be integrated.

Furthermore, the three through holes formed by the three first petals 25 are always open in the above-described embodiment. However, a cover member (not shown) having transparency and being pivotally attached to the outer surface of each of the hole pattern portions 22a and 22b may be formed on the outer surface of the mask main body 6. In this case, the above-mentioned three through holes can be opened, closed, or set in an intermediate state between them by pivoting the cover member. This makes it possible to adjust ventilation in the mask main body 6.

Those skilled in the art will recognize, or be able to ascertain using no more than routine experimentation, many equivalents to the specific embodiments of the invention described herein. Such equivalents are intended to be encompassed by the following claims.

The invention claimed is:

1. A gas supply mask apparatus comprising:
a mask main body wearable on the head of a mask wearer; and
a first connector comprising:
 a gas introduction opening capable of introducing a gas to a gas introduction space existing between a face of the mask wearer and the mask main body,
 a cylindrical portion extending substantially along a direction in which the gas introduction opening faces, and
 a substantially pyramidal upper-end surface portion formed on an upper end of the cylindrical portion such that it projects into the gas introduction space;
wherein:
the gas introduction opening is formed in a substantially central portion of the substantially pyramidal upper-end surface portion; and
when the mask main body is placed upward on a horizontal surface, a first angle within a range of 30° to 60° is formed between the horizontal surface and the direction in which the gas introduction opening faces.

2. The apparatus of claim 1, wherein the first angle falls within a range of 35° to 55°.

3. The apparatus of claim 1, wherein the first angle falls within a range of 40° to 50°.

4. The apparatus of claim 1, wherein, when the mask main body is placed upward on a horizontal surface and viewed from above, a second angle falling within a range of 0° to 15° is formed between the direction which the gas introduction opening faces and a central line bisecting the mask main body into left and right halves.

5. The apparatus of claim 4, wherein the second angle falls within a range of 0° to 10°.

6. The apparatus of claim 4, wherein the second angle falls within a range of 0° to 5°.

7. The apparatus of claim 1, further comprising a second connector connected to the first connector, the second connector comprising an upper cylindrical portion integrated with a lower cylindrical portion such that the upper cylindrical portion extends obliquely upward in a bent state from the lower cylindrical portion, which extends substantially downward, and
the upper cylindrical portion is configured to be pivotable with respect to the first connector.

8. The apparatus of claim 1, wherein a length of the cylindrical portion in the axial direction falls within a range of 12 to 24 mm, an inside area of the cylindrical portion in a direction substantially perpendicular to the axial direction falls within a range of 140 to 290 mm$^2$, and an opening area of the gas introduction opening falls within a range of 4.8 to 9.2 mm$^2$.

9. The apparatus of claim 8, wherein the cylindrical portion has a substantially circular cylindrical shape, an inner diameter of the cylindrical portion of the first connector falls within a range of 10 to 20 mm, the gas introduction opening has a substantially circular shape, and the diameter of the gas introduction opening falls within a range of 2 to 4 mm.

10. The apparatus of claim 1, wherein the apparatus is an oxygen mask apparatus.

11. The apparatus of claim 1,
wherein, when the mask is worn correctly by a mask wearer facing right forward and is viewed from the right side, a third angle within a range of 30° to 60° is formed between the direction in which the gas introduction opening faces and a virtual vertical plane facing right forward.

12. The apparatus of claim 11, wherein the third angle falls within a range of 35° to 55°.

13. The apparatus of claim 11, wherein the third angle falls within a range of 40° to 50°.

14. The apparatus of claim 11, wherein, when the mask is worn correctly by a mask wearer and is viewed right frontways, a fourth angle within a range of 0° to 15° is formed between the direction in which the gas introduction opening faces and a central line bisecting the mask main body into left and right halves.

15. The apparatus of claim 14, wherein the fourth angle falls within a range of 0° to 10°.

16. The apparatus of claim 14, wherein the fourth angle falls within a range of 0° to 5°.

17. The apparatus of claim 11, further comprising a second connector connected to the first connector, the second connector comprising an upper cylindrical portion integrated with a lower cylindrical portion, such that the upper cylindrical portion extends obliquely upward in a bent state from the lower cylindrical portion, which extends substantially downward, and the upper cylindrical portion is configured to be pivotable with respect to the first connector.

18. The apparatus of claim 11, wherein a length of the cylindrical portion in the axial direction falls within a range of 12 to 24 mm, an inside area of the cylindrical portion in a direction substantially perpendicular to the axial direction falls within a range of 140 to 290 mm$^2$, and an opening area of the gas introduction opening falls within a range of 4.8 to 9.2 mm$^2$.

19. The apparatus of claim 18, wherein the cylindrical portion has a substantially circular cylindrical shape, an inner diameter of the cylindrical portion of the first connector falls within a range of 10 to 20 mm, the gas introduction opening has a substantially circular shape, and the diameter of the gas introduction opening falls within a range of 2 to 4 mm.

20. The apparatus of claim 11, wherein the apparatus is an oxygen mask apparatus.

* * * * *